(12) United States Patent
Shandilya et al.

(10) Patent No.: US 9,914,770 B2
(45) Date of Patent: Mar. 13, 2018

(54) CLONING, EXPRESSION AND PURIFICATION METHOD FOR THE PREPARATION OF RANIBIZUMAB

(71) Applicant: INTAS PHARMACEUTICALS LTD, Gujarat (IN)

(72) Inventors: Harish Shandilya, Gujarat (IN); Himanshu Gadgil, Gujarat (IN); Vivek Farkade, Gujarat (IN)

(73) Assignee: INTAS Pharmaceuticals Ltd, Ahmedabad (IN)

( * ) Notice: Subject to any disclaimer, the term of this patent is extended or adjusted under 35 U.S.C. 154(b) by 70 days.

(21) Appl. No.: 14/787,981

(22) PCT Filed: Apr. 28, 2014

(86) PCT No.: PCT/IN2014/000274
§ 371 (c)(1),
(2) Date: Oct. 29, 2015

(87) PCT Pub. No.: WO2014/178078
PCT Pub. Date: Nov. 6, 2014

(65) Prior Publication Data
US 2016/0289314 A1 Oct. 6, 2016

(30) Foreign Application Priority Data
Apr. 30, 2013 (IN) .......................... 1570/MUM/2013

(51) Int. Cl.
| | | |
|---|---|---|
| *C07K 16/22* | (2006.01) | |
| *C07K 1/36* | (2006.01) | |
| *C07H 21/04* | (2006.01) | |
| *C12N 1/20* | (2006.01) | |
| *C12N 15/61* | (2006.01) | |
| *C12N 15/64* | (2006.01) | |

(52) U.S. Cl.
CPC .............. *C07K 16/22* (2013.01); *C07K 1/36* (2013.01); *C07K 2317/10* (2013.01); *C07K 2317/14* (2013.01); *C07K 2317/24* (2013.01); *C07K 2317/51* (2013.01); *C07K 2317/515* (2013.01); *C07K 2317/55* (2013.01); *C07K 2317/76* (2013.01)

(58) Field of Classification Search
CPC ...... C07K 16/22; C07K 1/36; C07K 2317/10; C07K 2317/14; C07K 2317/24; C07K 2317/51; C07K 2317/515; C07K 2317/55; C07K 2317/76; C07H 21/04; C12N 1/20; C12N 15/61; C12N 2830/002
See application file for complete search history.

(56) References Cited

U.S. PATENT DOCUMENTS

| | | | |
|---|---|---|---|
| 5,641,870 A | 6/1997 | Rinderknecht et al. | |
| 6,217,866 B1 * | 4/2001 | Schlessinger | A61K 39/395 424/130.1 |
| 6,979,556 B2 * | 12/2005 | Simmons | C07K 16/22 435/252.3 |
| 6,998,383 B2 | 2/2006 | Aggarwal et al. | |
| 7,569,384 B2 | 8/2009 | Rosen et al. | |
| 7,847,071 B2 | 12/2010 | Bonnerjea et al. | |
| 8,597,907 B2 | 12/2013 | Date et al. | |
| 2005/0037456 A1 * | 2/2005 | Lester | C12P 21/02 435/69.1 |
| 2009/0311750 A1 * | 12/2009 | West | C07K 16/00 435/69.6 |
| 2010/0227905 A1 * | 9/2010 | Kabra | A61K 9/0048 514/407 |
| 2010/0322931 A1 * | 12/2010 | Harding | C07K 16/22 424/134.1 |
| 2013/0197197 A1 | 8/2013 | Eckermann et al. | |

FOREIGN PATENT DOCUMENTS

| | | |
|---|---|---|
| WO | 02056910 | 7/2002 |
| WO | 2009021548 | 2/2009 |
| WO | 2010148223 | 12/2010 |
| WO | 2011089212 | 7/2011 |

OTHER PUBLICATIONS

Tan et al., Protein Expression and Purification 25: 430-436, 2002.*
International Search Report for PCT/IN2014/000274, Completed by the Indian Patent Office on Oct. 14, 2014, 5 Pages.
Choi et al. Appl Microbiol Biotechnol 2004, vol. 64, p. 625-635, "Secretory and extracellular production of recombinant proteins using *Escherichia coli*".
Liu et al. mAbs Sep./ Oct. 2010, vol. 2, Issue 5, p. 480-499, "Recovery and purification process development for monoclonal antibody production".
Tan et al. Protein Expression and Purification 2002 vol. 25, p. 430-436, "Efficient expression and secretion of recombinant hirudin III in *E. coli* using the L-asparaginase II signal sequence".
Lien et al. Handbook of Experimental Pharmacology 2008, vol. 181, pp. 131-150, "Therapeutic Anti-VEGF Antibodies".

* cited by examiner

*Primary Examiner* — Phuong Huynh
(74) *Attorney, Agent, or Firm* — Brooks Kushman P.C.

(57) ABSTRACT

A polynucleotide sequence and a method for Ranibizumab cloning, expression and production having better yield and biologically active protein.

7 Claims, 5 Drawing Sheets

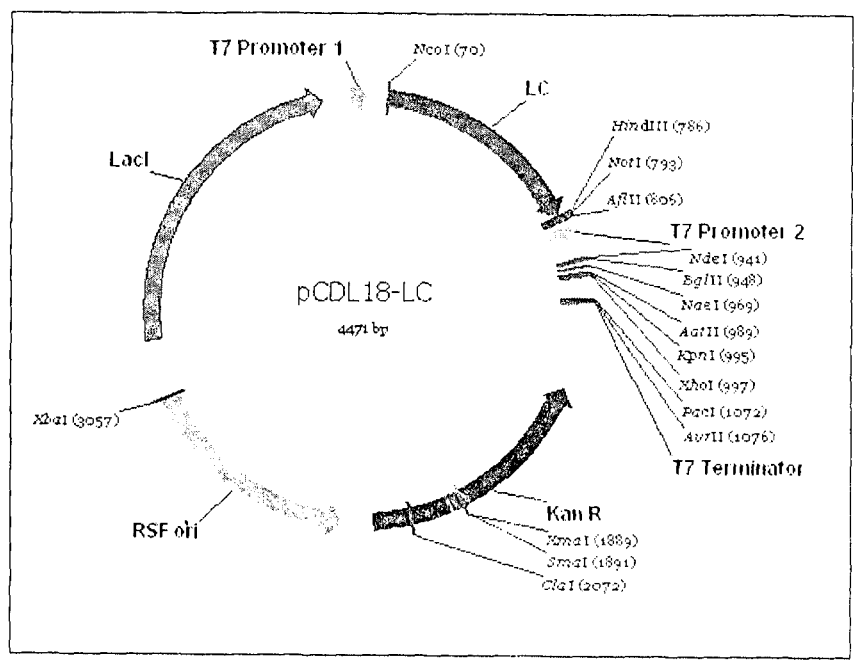
Figure – 1: pCDL18-LC vector carrying Ranibizumab Light Chain gene

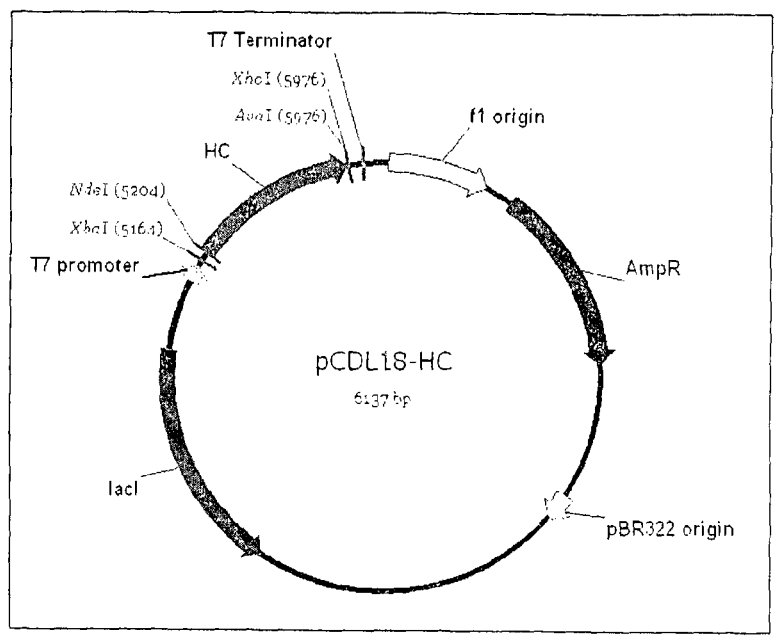
Figure – 2: pCDL18-HC vector carrying Ranibizumab Heavy Chain gene

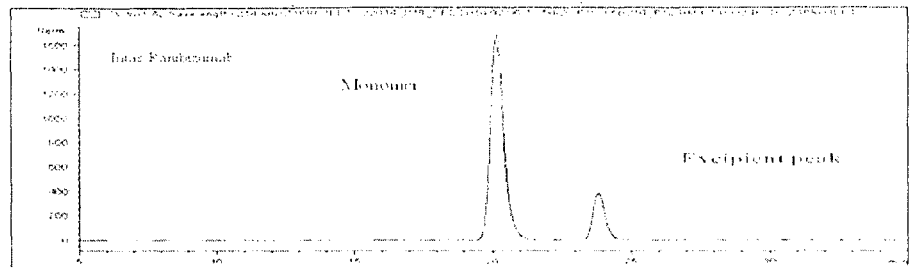
SEC-HPLC profile of Intas Ranibizumab (99.9 % purity)
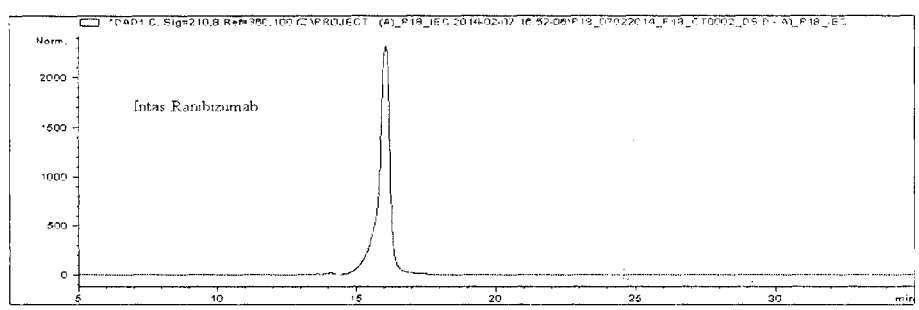
CEX-HPLC profile of Intas Ranibizumab (98.7 % purity)
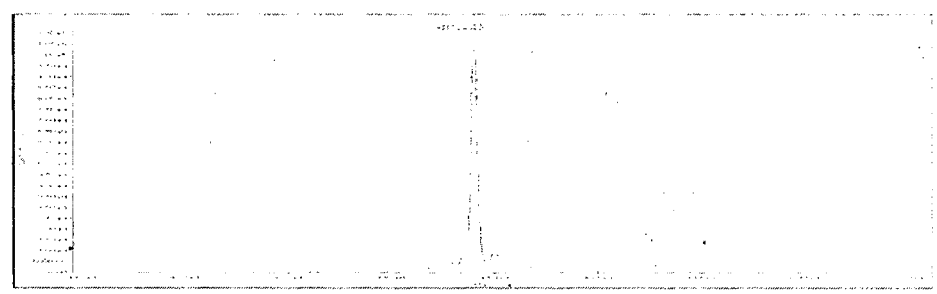
Mass spectra profile of Intas Ranibizumab (48.38kDa)
Figure – 3: Characterization of recombinant protein expressed using above process

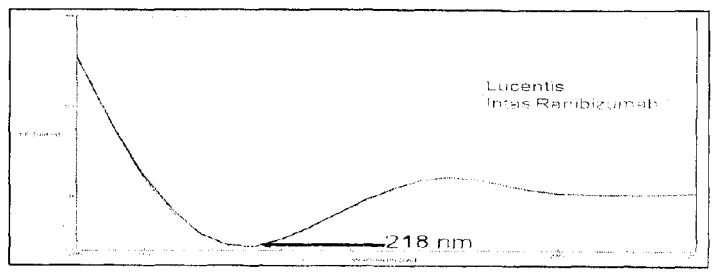
Figure – 4a: CD Spectra of properly folded Ranibizumab compared with Lucentis
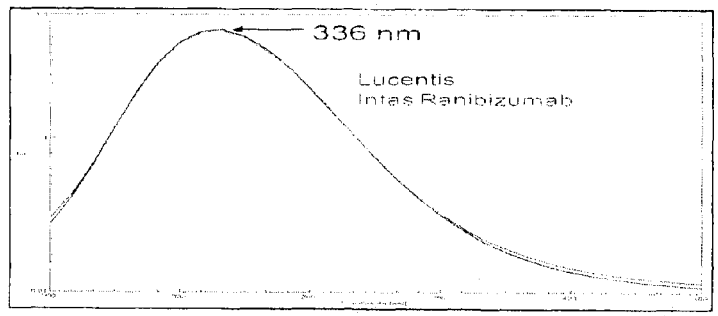
Figure – 4b: Fluorescence Spectra of properly folded Ranibizumab compared with Lucentis

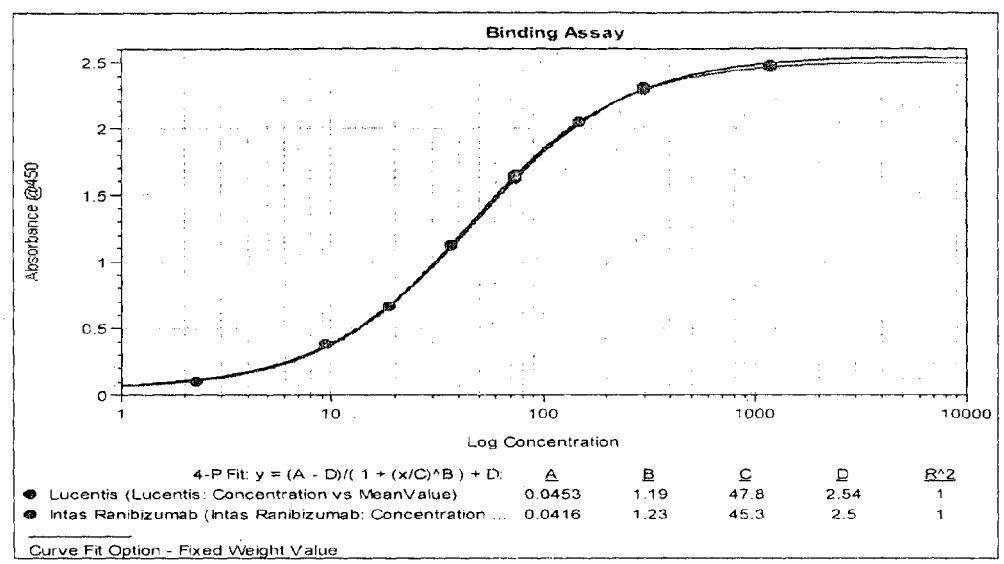
Figure – 5: Cell based assay showing comparative potency of recombinant Ranibizumab compared with Lucentis // CLONING, EXPRESSION AND PURIFICATION METHOD FOR THE PREPARATION OF RANIBIZUMAB

CROSS-REFERENCE TO RELATED APPLICATION

This application is the U.S. national phase of PCT Application No. PCT/IN2014/000274 filed on Apr. 28, 2014, which claims priority to IN Patent Application No. 1570/MUM/2013 filed on Apr. 30, 2013, the disclosures of which are incorporated in their entirety by reference herein.

SEQUENCE LISTING

The text file sequence 003.txt of size 8 KB created Sep. 11, 2017, filed herewith, is hereby incorporated by reference.

FIELD OF THE INVENTION

The present invention relates to Ranibizumab cloning, expression and production using a novel approach for better yield and biologically active protein.

BACKGROUND OF THE INVENTION

Proteins are important as these are used to cure a number of diseases including angiogenesis (VEGF) diabetes (e.g. Insulin), cancers (e.g. Interferon, monoclonal antibodies), heart attacks, strokes, cystic fibrosis (e.g. Enzymes, Blood factors), inflammation diseases (e.g. Tumor Necrosis Factors), anemia (e.g. Erythropoietin), hemophilia (e.g. Blood clotting factors) etc. One of the important challenges is the development of efficient and competent process for the cloning, expression and large scale purification of these proteins. Numerous processes are available for the cloning, expression and large scale purification of desired protein from the cell culture supernatants, but still it is difficult to clone, express and separate the desired protein from the mixture.

Vascular endothelial growth factor A (VEGF-A) is a biological component that can trigger angiogenesis, which is the growth of new blood vessels. Various diseases, inter alia, ischemia, anemia, peripheral vascular disease, and atherosclerotic lesions can be treated by increasing angiogenesis. This is accomplished by stimulating the up-regulation of VEGF-A, thereby leading to increased blood circulation, hence increased oxygen supply, in the diseased tissue. In the eye, however, excessive vascularization can result in blood and fluid leaking into the eye. These leaky blood vessels can contribute to macular edema and choroidal neovascularization, resulting in the wet type of age-related macular degeneration (AMD). The result of AMD can be the loss of visual acuity or even blindness. Therefore, control of excessive macular vascularization is important in the treatment of macular degeneration. As such, it is a goal of medical professionals to provide a treatment for controlling or curing AMD without inhibiting the beneficial effects of normal VEGF-A activity in the rest of the body. Ranibizumab has been found to be an effective treatment of AMD.

Ranibizumab is a recombinant humanized IgGI kappa isotype monoclonal antibody that inhibits VEGF activity by competitively binding to the receptor binding site of active forms of VEGF-A, including the biologically active, cleaved form of this molecule, VEGF110. Hence, Ranibizumab prevents binding of VEGF-A to its principle receptors VEGFR1 and VEGFR2 found on the surface of endothelial cells. This results in reduced endothelial cell proliferation, vascular leakage, and new blood vessel formation.

LUCENTIS® is a medical formulation of Ranibizumab and designed for intraocular injection directly into the vitreous humor of the eye, wherein the active ingredient Ranibizumab penetrates the internal limiting membrane to access the subretinal space. These injections are typically given from 5 to 7 times a year to patients and in many instances are given monthly. Since the cost of treatment is very high and not many patients can afford it as such, there is still a need for improved cloning process and purification of the protein so that the production efficiency can be enhanced and the drug can be produced cheaper.

U.S. Pat. No. 6,998,383 discloses RANK inhibitor consisting of a TRAF-6 binding domain attached to a leader sequence.

U.S. Pat. No. 7,569,384 discloses nucleic acid molecule encoding albumin fusion protein. Also discloses vectors containing these nucleic acids, host cell transformed with these nucleic acid vectors and methods of making the albumin fusion protein using these nucleic acids, vectors and/or host cell.

U.S. Pat. No. 8,597,907 discloses a method for efficiently producing an industrially useful protein in coryneform bacteria. The present invention provides a method for efficiently producing heterologous proteins comprising culturing coryneform bacteria containing an genetic construction containing a promoter sequence which functions in coryneform bacteria, a nucleic acid sequence encoding a Tat system-dependent signal peptide region, and a nucleic acid sequence encoding a heterologous protein, in the direction from 5'-end to 3'-end, and secretory producing the heterologous protein by coryneform bacteria.

U.S. Pat. No. 5,641,870 discloses a process for purifying an antibody. In this process, a mixture containing the antibody and contaminant is subjected to low pH hydrophobic interaction chromatography (LPHIC) optionally at low salt concentration. The antibody is eluted from the column in the fraction which does not bind thereto. This process can be preceded and followed by other purification steps.

U.S. Pat. No. 7,847,071 discloses a method of purifying an antibody comprising the steps of: firstly, purifying an antibody by means of protein A affinity chromatography wherein the protein A is a native protein A or a functional derivative thereof, secondly, loading the purified antibody comprising a protein A-contaminant, wherein said protein A-contaminant is obtained upon eluting bound antibody from said protein A affinity chromatography, on a first ion exchanger under conditions which allow for binding of the protein A or its derivative, thirdly, collecting the antibody loaded onto the first ion exchanger in the flow-through of the first ion exchanger whilst a contaminant protein A is bound to the first ion exchanger, wherein the first ion exchanger is an anion exchanger, further purifying the antibody by loading on, binding to and eluting it from a second ion exchanger, and discarding a tail fraction of the eluate of the second ion exchanger such that a monomeric antibody fraction is enriched as a purified antibody pool.

WO2011089212 discloses a method for depleting impurities, in particular host cell proteins (HCP) and DNA from cell culture supernatants by means of protein A chromatography using a novel washing buffer.

Liu et al., discussed in mAbs 2, 2010, 480-499 about the basic unit operations such as harvest, Protein A affinity chromatography and additional polishing steps along with alternative processes such as flocculation, precipitation and membrane chromatography and also covered platform approaches to purification methods development, use of high throughput screening methods, and offered a view on future developments in purification methodology as applied to monoclonal antibodies.

Refolding of inclusion body proteins into bioactive forms is cumbersome, requires many operational steps and most of the time results in very low recovery of refolded protein. In the cases where a high yielding recovery process has been developed for refolding of the aggregated protein, inclusion body formation provides a straight forward strategy for recombinant protein purification. The higher the amount of this partially folded protein that is converted into the bioactive form, the more therapeutic protein can be recovered with improved yield and at low cost from inclusion bodies of *E. coli*.

It is necessary to have a method for the cloning, expression and purification of antibodies and preferably without cost-intensive chromatographic steps as well as extensive steps. The antibody obtained by the cloning, expression and purification method according to the present invention is supposed to meet the criteria for purity & yield which are set forth by the admission authorities.

OBJECT OF THE INVENTION

The principal object of the present invention is to use novel cloning processes followed by novel protein expression and its purification procedures for rapid and efficient recovery of recombinant Ranibizumab.

It is an object of the present invention to provide novel cloning process of Ranibizumab which comprises transforming the host cell with:
i) the vector comprising nucleic acid sequence of SEQ ID No. 1 encoding for light chain of Ranibizumab having an amino acid sequence as shown in SEQ ID No. 2 wherein N-terminal of the said SEQ ID No. 1 is operably linked to a unique signal sequence, start codon and an inducible promoter system
ii) transforming another host cell with another plasmid vector comprising nucleic acid sequence of SEQ ID No. 3 encoding for heavy chain of Ranibizumab having an amino acid sequence as shown in SEQ ID No. 4 wherein N-terminal of the said SEQ ID No. 3 is operably linked to a unique signal sequence, start codon and an inducible promoter system.

Another object of the present invention is to provide novel protein expression method for the preparation of Ranibizumab which comprises steps of:
i) expressing light & heavy chain separately in two different expression host cells
ii) exporting protein to the periplasmic space of the cells with the help of a unique signal sequence
iii) partially pure light and heavy chain proteins are refolded together in-vitro Yet another object of the present invention is to provide novel protein purification method of Ranibizumab having an amino acid sequence of SEQ. ID. No. 2 and 4, which comprises:
i) high cell density culturing of the host cells in a growth medium by maintaining specific culture conditions
ii) expression of the protein in the form of periplasmic inclusion bodies
iii) protein refolding of both chains together in-vitro
iv) purification of correctly folded protein Yet another object of the present invention is to provide improved purification process of Ranibizumab which comprises:

i) in-vitro refolding of protein
ii) performing anion exchange chromatography to separate out closely related misfolded protein species
iii) performing cation exchange Chromatography followed by
iv) ultra filtration/Diafiltration Further object of the present invention is to provide improved purification process of Ranibizumab which is capable to separate out even closely related misfolded protein species (>95% pure protein).

Yet another object of the invention is to provide a nucleic acid sequence of SEQ ID No. 1 which encodes for light chain of Ranibizumab wherein N-terminal of the said SEQ ID No. 1 is operably linked to a unique signal sequence (SEQ ID No. 5).

Yet another object of the invention is to provide a nucleic acid sequence of SEQ ID No. 3 which encodes for heavy chain of Ranibizumab wherein N-terminal of the said SEQ ID No. 3 is operably linked to a unique signal sequence (SEQ ID No. 6).

Yet another object of the invention is to provide use of unique signal sequence containing the amino acid sequence of SEQ ID No. 5 for production of anti-VEGF antibody.

Yet another object of the invention is to provide use of a unique signal sequence containing the amino acid sequence of SEQ ID No. 6 for production of anti-VEGF antibody.

Yet another object of the invention is to provide use of a unique signal sequence containing the amino acid sequence of SEQ ID No. 5 for production of light chain of Ranibizumab.

Yet another object of the invention is to provide use of a unique signal sequence containing the amino acid sequence of SEQ ID No. 6 for production of heavy chain of Ranibizumab.

SUMMARY OF THE INVENTION

The principal aspect of the present invention is to use novel cloning processes followed by novel protein expression and its purification procedures for rapid and efficient recovery of recombinant Ranibizumab.

It is an aspect of the present invention to provide novel cloning process of Ranibizumab which comprises transforming the host cell with:
i) the vector comprising nucleic acid sequence of SEQ ID No. 1 encoding for light chain of Ranibizumab having an amino acid sequence as shown in SEQ ID No. 2 wherein N-terminal of the said SEQ ID No. 1 is operably linked to a unique signal sequence, start codon and an inducible promoter system
ii) transforming another host cell with another plasmid vector comprising nucleic acid sequence of SEQ ID No. 3 encoding for heavy chain of Ranibizumab having an amino acid sequence as shown in SEQ ID No. 4 wherein N-terminal of the said SEQ ID No. 3 is operably linked to a unique signal sequence, start codon and an inducible promoter system.

Another aspect of the present invention is to provide novel protein expression method for the preparation of Ranibizumab which comprises steps of:
i) expressing light & heavy chain separately in two different expression host cells
ii) exporting protein to the periplasmic space of the cells with the help of a unique signal sequence
iii) partially pure light and heavy chain proteins are refolded together in-vitro Yet another aspect of the present invention is to provide novel protein purification method of Ranibizumab having an amino acid sequence of SEQ. ID. No. 2 and 4, which comprises:
i) high cell density culturing of the host cells in a growth medium by maintaining specific culture conditions
ii) expression of the protein in the form of periplasmic inclusion bodies
iii) protein refolding of both chains together in-vitro
iv) purification of correctly folded protein Yet another aspect of the present invention is to provide improved purification process of Ranibizumab which comprises:
i) in-vitro refolding of protein
ii) performing anion exchange chromatography to separate out closely related misfolded protein species
iii) performing cation exchange Chromatography followed by
iv) ultra filtration/Diafiltration. Yet another aspect of the present invention is a process comprising the reduction, oxidation and subsequent in-vitro refolding of the solubilized inclusion bodies to recover biologically active Ranibizumab wherein the purification process comprises the following steps: ultrafiltration & diafiltration-I, anion exchange chromatography, cation exchange chromatography, ultrafiltration & diafiltration-II, and 0.2 µm filtration.

Further aspect of the present invention is to provide improved purification process of Ranibizumab which is capable to separate out even closely related misfolded protein species (>95% pure protein).

Yet another aspect of the invention is to provide a nucleic acid sequence of SEQ ID No. 1 which encodes for light chain of Ranibizumab wherein N-terminal of the said SEQ ID No. 1 is operably linked to a unique signal sequence (SEQ ID No. 5).

Yet another aspect of the invention is to provide a nucleic acid sequence of SEQ ID No. 3 which encodes for heavy chain of Ranibizumab wherein N-terminal of the said SEQ ID No. 3 is operably linked to a unique signal sequence (SEQ ID No. 6).

Yet another aspect of the invention is to provide use of unique signal sequence containing the amino acid sequence of SEQ ID No. 5 for production of anti-VEGF antibody.

Yet another aspect of the invention is to provide use of a unique signal sequence containing the amino acid sequence of SEQ ID No. 6 for production of anti-VEGF antibody.

Yet another aspect of the invention is to provide use of a unique signal sequence containing the amino acid sequence of SEQ ID No. 5 for production of light chain of Ranibizumab.

Yet another aspect of the invention is to provide use of a unique signal sequence containing the amino acid sequence of SEQ ID No. 6 for production of heavy chain of Ranibizumab.

BRIEF DESCRIPTION OF THE FIGURES

FIG. 1 represents expression plasmid carrying Ranibizumab light chain gene construct
FIG. 2 represents expression plasmid carrying Ranibizumab heavy chain gene construct
FIG. 3 represents characterization of recombinant protein expressed using above process
FIG. 4a represents CD Spectra of properly folded Ranibizumab compared with Lucentis
FIG. 4b represents fluorescence Spectra of properly folded Ranibizumab compared with Lucentis
FIG. 5 represents cell based assay showing comparative potency of recombinant Ranibizumab compared with Lucentis

DETAILED DESCRIPTION OF THE INVENTION

Ranibizumab is an affinity maturated Fab fragment derived from bevacizumab. Ranibizumab has a higher affinity for VEGF and also is smaller in size, allowing it to better penetrate the retina, and thus treat the ocular neovascularization associated with AMD (Lien and Lowman, In: Chemajovsky, 2008, Therapeutic Antibodies. Handbook of Experimental Pharmacology 181, Springer-Verlag, Berlin Heidelberg 131-150). Ranibizumab was developed and is marketed by Genentech under the trade name Lucentis.

LUCENTIS is a sterile, colorless to pale yellow solution in a single-use glass vial. Ranibizumab, which lacks an Fc region, has a molecular weight of approximately 48 kilodaltons and is produced by an *E. coli* expression system in a nutrient medium containing the antibiotic tetracycline. Tetracycline is not detectable in the final product.

Unless indicated otherwise, the term "VEGF-binding molecule" includes anti-VEGF antibodies, anti-VEGF antibody fragments, "anti-VEGF antibody-like molecules" and conjugates with any of these. Antibodies include, but are not limited to, monoclonal and chimerized monoclonal antibodies. The term "antibody" encompasses complete immunoglobulins, like monoclonal antibodies produced by recombinant expression in host cells, as well as VEGF-binding antibody fragments or "antibody-like molecules", including single-chain antibodies and linear antibodies, so-called "SMIPs" ("Small Modular Immunopharmaceuticals"), as e.g. described in WO002/056910. Anti-VEGF antibody-like molecules include immunoglobulin single variable domains, as defined herein. Other examples for antibody-like molecules are immunoglobulin super family antibodies (IgSF), or CDR-grafted molecules.

"VEGF-binding molecule" refers to both monovalent VEGF-binding molecules (i.e. molecules that bind to one epitope of VEGF) as well as to bi- or multivalent binding molecules (i.e. binding molecules that bind to more than one epitope, e.g. "biparatopic" molecules as defined hereinbelow).

Signal sequence refers to a sequence present on the N-terminal side of a secretory protein precursor but absent in the naturally-occurring mature protein, and a "signal peptide" refers to a peptide cleaved from such a protein precursor. In general, a signal sequence is cleaved by a protease (typically referred to as a signal peptidase) when secreted extracellularly. Although such signal peptides have constant, common features in their sequences among biological species, a signal peptide which exhibits a secretory function in a certain biological species does not necessarily exhibit a secretory function in another biological species.

Inclusion bodies are dense electron-refractile particles of aggregated protein found in both the cytoplasmic and periplasmic spaces of *E. coli* during high-level expression of heterologous protein. It is generally assumed that high level expression of non-native protein (higher than 2% of cellular protein) and highly hydrophobic protein is more prone to lead to accumulation as inclusion bodies in *E. coli*. In the case of proteins having disulfide bonds, formation of protein aggregates as inclusion bodies is anticipated since the reducing environment of bacterial cytosol inhibits the formation of disulfide bonds.

Inclusion bodies have higher density (~1.3 mg ml-1) than many of the cellular components, and thus can be easily separated by high-speed centrifugation after cell disruption. Expression of recombinant proteins as inclusion bodies in bacteria is one of the most efficient ways to produce cloned proteins, as long as the inclusion body protein can be successfully refolded. Aggregation is the leading cause of decreased refolding yields.

Protein refolding refers to the process by which a protein structure assumes its functional shape or conformation. It is the physical process by which a polypeptide folds into its characteristic and functional three-dimensional structure from random coil. Each protein exists as an unfolded polypeptide or random coil when translated from a sequence of mRNA to a linear chain of amino acids. This polypeptide lacks any stable (long-lasting) three-dimensional structure. Amino acids interact with each other to produce a well-defined three-dimensional structure, the folded protein, known as the native state. The resulting three-dimensional structure is determined by the amino acid sequence. Insoluble, inactive inclusion bodies are frequently formed upon recombinant protein production in transformed microorganisms. These inclusion bodies, which contain the recombinant protein in an highly enriched form, can be isolated by solid/liquid separation. After solubilization, native proteins can be generated from the inactive material by using in vitro folding techniques.

The present invention provides new refolding procedure for Ranibizumab comprising efficient in vitro reconstitution of complex hydrophobic, multidomain, oligomeric, or highly disulfide-bonded proteins. These protocols take into account process parameters such as protein concentration, catalysis of disulfide bond formation, temperature, pH, and ionic strength, as well as specific solvent ingredients that reduce unproductive side reactions.

Clone refers to a DNA sequence, such as a gene, that is transferred from one organism to another and replicated by genetic engineering techniques. The present invention comprises genes of heavy and light chain of Ranibizumab with desired modifications for cloning on both the ends. The gene sequences are optimized for better protein expression in *E. coli*. The synthetic constructs are made so as to have a bacterial leader signal sequence at the N-terminal followed by sequences of gene of interest and two translation stop codons in the end. These signal sequences are selected on the basis of their ability so that they can transport maximum protein in the periplasm of the cell. The signal sequence chosen was taken from a natural bacterial gene.

The main embodiment of the present invention is to use novel cloning processes followed by novel protein expression and its purification procedures for rapid and efficient recovery of recombinant Ranibizumab.

It is yet another embodiment of the present invention to provide novel cloning process of Ranibizumab which comprises transforming the host cell with:
i) the vector comprising nucleic acid sequence of SEQ ID No. 1 encoding for light chain of Ranibizumab having an amino acid sequence as shown in SEQ ID No. 2 wherein N-terminal of the said SEQ ID No. 1 is operably linked to a unique signal sequence, start codon and an inducible promoter system
ii) transforming another host cell with another plasmid vector comprising nucleic acid sequence of SEQ ID No. 3 encoding for heavy chain of Ranibizumab having an amino acid sequence as shown in SEQ ID No. 4 wherein N-terminal of the said SEQ ID No. 3 is operably linked to a unique signal sequence, start codon and an inducible promoter system.

Another embodiment of the present invention is to provide novel protein expression method for the preparation of Ranibizumab which comprises steps of:
i) expressing light & heavy chain separately in two different expression host cells
ii) exporting protein to the periplasmic space of the cells with the help of a unique signal sequence
iii) partially pure light and heavy chain proteins are refolded together in-vitro.

Another embodiment of the present invention is to provide novel protein purification method of Ranibizumab having an amino acid sequence of SEQ. ID. No. 2 and 4, which comprises:
i) high cell density culturing of the host cells in a growth medium by maintaining specific culture conditions
ii) expression of the protein in the form of periplasmic inclusion bodies
iii) protein refolding of both chains together in-vitro
iv) purification of correctly folded protein Yet another embodiment of the present invention is to provide improved purification process of Ranibizumab which comprises:
i) in-vitro refolding of protein
ii) performing anion exchange chromatography to separate out closely related misfolded protein species
iii) performing cation exchange Chromatography followed by
iv) ultra filtration/Diafiltration Yet another embodiment of the present invention is to provide improved purification process of Ranibizumab which is capable to separate out even closely related misfolded protein species (>95% pure protein).

Yet another embodiment of the invention is to provide a nucleic acid sequence of SEQ ID No. 1 which encodes for light chain of Ranibizumab wherein N-terminal of the said SEQ ID No. 1 is operably linked to a unique signal sequence (SEQ ID No. 5).

Yet another embodiment of the invention is to provide a nucleic acid sequence of SEQ ID No. 3 which encodes for heavy chain of Ranibizumab wherein N-terminal of the said SEQ ID No. 3 is operably linked to a unique signal sequence (SEQ ID No. 6).

Yet another embodiment of the invention is to provide use of unique signal sequence containing the amino acid sequence of SEQ ID No. 5 for production of anti-VEGF antibody.

Yet another embodiment of the invention is to provide use of a unique signal sequence containing the amino acid sequence of SEQ ID No. 6 for production of anti-VEGF antibody.

Yet another embodiment of the invention is to provide use of a unique signal sequence containing the amino acid sequence of SEQ ID No. 5 for production of light chain of Ranibizumab.

Yet another embodiment of the invention is to provide use of a unique signal sequence containing the amino acid sequence of SEQ ID No. 6 for production of heavy chain of Ranibizumab.

Light Chain Nucleotide Sequence
(SEQ ID NO: 1)
5' GAGCT*CCATG*GAGTTTTTCAAAAAGACGGCACTTGCCGCACTGGTT

ATGGGTTTTAGTGGTCCAGCATTGGCCGATATCCAGCTGACCCAGAGCC

-continued
```
CGAGCAGCCTGAGCGCAAGCGTTGGTGATCGTGTTACCATTACCTGTAG

CGCAAGCCAGGATATTAGCAATTATCTGAATTGGTATCAGGAGAAACCG

GGTAAAGCACCGAAAGTTCTGATTTATTTTACCAGGAGCCTGCATAGCG

GTGTTCCGAGCCGTTTTAGCGGTAGCGGTAGTGGCACCGATTTTACCCT

GACCATTAGCAGCCTGCAGCCGGAAGATTTTGCAACCTATTATTGTCAG

CAGTATAGCACCGTTCCGTGGACCTTTGGTCAGGGCACCAAAGTTGAAA

TTAAACGTACCGTTGCAGCACCGAGCGTTTTTATTTTTCCGCCTAGTGA

TGAACAGCTGAAAAGCGGCACCGCAAGCGTTGTTTGTCTGCTGAATAAT

TTTTATCCGCGTGAAGCAAAAGTGCAGTGGAAAGTTGATAATGCACTGC

AGAGCGGTAATAGCCAAGAAAGCGTTACCGAACAGGATAGCAAAGATAG

CACCTATAGCCTGAGCAGCACCCTGACCCTGAGCAAAGCAGATTATGAA

AAACACAAAGTGTATGCCTGCGAAGTTACCCATCAGGGTCTGAGCAGTC

CGGTTACCAAAAGTTTTAATCGTGGCGAATGCTAATAGAAGCTTGGTA

CC 3'
```
Light Chain Amino acid Sequence
(SEQ ID NO: 2)
```
DIQLTQSPSSLSASVGDRVTITCSASQDISNYLNWYQQKPGKAPKVLIY

FTSSLIISGVPSRFSGSGSGTDFTLTISSLQPEDFATYYCQQYSTVPWT

FGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC
```
Heavy Chain Nucleotide Sequence
(SEQ ID NO: 3)
```
5' GAGCTCATATGAAATACCTGCTGCCGACCGCTGCTGCTGGTCTGCT

GCTCCTCGCTGCCCAGCCGGCGATGGCCGAAGTTCAGCTGGTTGAAAGC

GGTGGTGGTCTGGTTCAGCCTGGTGGTAGCCTGCGTCTGAGCTGTGCAG

CAAGCGGTTATGATTTTACCCATTATGGTATGAATTGGGTTCGTCAGGC

ACCGGGTAAAGGTCTGGAATGGGTTGGTTGGATTAATACCTATACCGGT

GAACCGACCTATGCAGCAGATTTTAAACGTCGTTTTACCTTTAGCCTGG

ATACCAGCAAAAGCACCGCATATCTGCAGATGAATAGCCTGCGTGCAGA

AGATACCGCAGTTTATTATTGTGCCAAATATCCGTATTACTATGGCACC

AGCCACTGGTATTTCGATGTTTGGGGTCAGGGCACCCTGGTTACCGTTA

GCAGCGCAAGCACCAAAGGTCCGAGCGTTTTTCCGCTGGCACCGAGCAG

CAAAAGTACCAGCGGTGGCACAGCAGCACTGGGTTGTCTGGTTAAAGAT

TATTTTCCGGAACCGGTTACCGTGAGCTGGAATAGCGGTGCACTGACCA

GCGGTGTTCATACCTTTCCGGCAGTTCTGCAGAGCAGCGGTCTGTATAG

CCTGAGCAGCGTTGTTACCGTTCCGAGCAGCAGCCTGGGCACCCAGACC

TATATTTGTAATGTTAATCATAAACCGAGCAATACCAAAGTGGATAAAA

AAGTTGAGCCGAAAAGCTGCGATAAAACCCATCTGTAATAGGGTACC 3'
```
Heavy Chain Amino acid Sequence
(SEQ ID NO: 4)
```
EVQLVESGGGLVQPGGSLRLSCAASGYDFTHYGNINWVRQAPGKGLEWV GWINTYTGEPTYAADFKRRFTFSLDTSKSTAYLQMINSLRAEDTAVYYC
```
-continued
```
AKYPYYYGTSHWYFDVWGQGTLVTVSSASTKGPSVFPLAPSSKSTSGGT

AALGCLVKDYFPEPVTVSWNSGALTSGVHTFPAVLQSSGLYSLSSVVTV

PSSSLGTQTVICNVNHKPSNTKVDKKVEPKSCDKTHL
```

The amino acid sequence of the unique signal sequence for light chain of Ranibizumab is:

(SEQ ID No: 5)
MEFFKKTALAALVMGFSGAALA

The amino acid sequence of the unique signal sequence for heavy chain of Ranibizumab is:

(SEQ ID No: 6)
MKYLLPTAAAGLLLLAAQPAMA

The invention will now be further described by the following examples, which are illustrative rather than limiting.

Example 1

Generation of pCDL18-LC Vector for Light Chain of Ranibizumab

Bacterial expression vector for light chain of Ranibizumab was generated by cloning light chain of Ranibizumab along with a signal sequence (SEQ ID No: 1) at the 5' end into the NcoI/HindIII site in multiple cloning site (MCS) of pCDL18-LC vector.

Key components of synthetic gene cassette and schematic design are as given below.

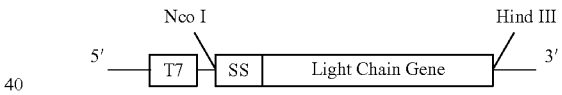

Generation of pCDL18-HC Vector for Heavy Chain of Ranibizumab

Bacterial expression vector for heavy chain of Ranibizumab was generated by cloning heavy chain of Ranibizumab along with a signal sequence (SEQ ID No: 3) at the 5' end into the NdeI/XhoI site in pCDL18-HC vector.

Key components of synthetic gene cassette and schematic design are as given below.

Example 2

Transformation of Light Chain Gene in BL21 (DE3)

pSR04 vector carrying expression construct for light chain gene (pCDL18-LC) was transformed in BL21 (DE3) and recombinant clones were selected. The transformants were plated on LB agar plates containing kanamycin (30 µg/ml) for selection. Protein expression analysis was also performed after inducing the cells with 1 mM IPTG for 4 h in a shake flask. Whole cell lysate and extracellular protein samples were analyzed for clone selection.

Transformation of Heavy Chain Gene in BL21 (DE3)

pSR02 vector carrying expression construct for heavy chain gene (pCDL18-HC) was transformed in BL21 (DE3) and recombinant clones were selected. The transformants were plated on LB agar plates containing ampicillin for selection. Protein expression analysis was also performed after inducing the cells with 1 mM IPTG for 4 h in a shake flask. Whole cell lysate and extracellular protein samples were analyzed for clone selection.

Example 3

General Expression of Light & Heavy Chain Separately in Two Different Expression Host Cells in *E. coli*

To maximize the desired protein expression the light and heavy chains of Ranibizumab were cloned into two separate vector systems and transformed individually in two different *E. coli* cells. The protein expression is derived from T7 promoter system. Both these constructs are carried in by these high copy number plasmids and capable of expressing protein in a tightly regulated manner.

The overexpressed recombinant proteins are purified and characterized. The first 10 residues at the N-terminal were confirmed to be DIQLTQSPSS (aa 1 to 10 of SEQ ID NO: 2) for light chain and EVQLVESGGG (aa 1 to 10 of SEQ ID NO: 4) for the heavy chain, which is the authentic start sequence of both the chains. A clear and unambiguous signal was obtained for all the 10 residues.

Example 4

Generation of Targeted Protein in Form of Periplasm Inclusion Bodies

The recombinant *E. coli* cells were cultivated in the shake flasks (seed flasks) for inoculum preparation and for production, the inoculum obtained from seed flask was transferred to production fermenter and cultured for 25 h in fed batch mode. During fermentation, the cells were provided with air and oxygen by means of sparging. The growth of the cells was maintained by controlled addition of feed (Nutrient supplements) in pH stat mode, the pH was maintained by supplying glucose and nitrogen in feed to reduce the pH of the batch. Base (NaOH) was used to increase the pH of the batch as needed. Cells were induced with IPTG at 20th hour of batch age and the fermentation is carried out for another 5 hours. The targeted protein is produced in the form of periplasmic IBs.

For light chain the cell culture density (OD600) at harvest was ~50 and biomass obtained from that was around 100 g/L, which yielded around 25 g IBs/L.

Similarly for heavy chain the cell culture density (OD600) at harvest was ~100 and biomass obtained was around 155 g/L which yielded around 33 g IBs/L.

Example 5

Refolding of Light and Heavy Chain Together 25 g of LC and HC each were solubilized separately in 500 mL of solubilization buffer containing 6 M GuHCl and pooled in 1:1 ratio. Pooled SIB was reduced with 4 mM of DTT for 1 h. Reduced LC and HC pool was subjected to oxidation with 10 mM cystine and incubated for 3 h. Reduced and oxidized SIB were diluted 25 times in the refolding buffer (100 mM Tris, 0.6 M Arginine, 5% Sorbitol, 2 mM EDTA, pH 9.0) by slow addition. The 0.6 mM of cystine and 0.75 mM of cysteine was added to the refolding mixture and reaction was incubated at (2-8)° C. for ~5 days Refolding output was concentrated using 10 kDa membrane and diafiltered against 50 mM Tris buffer, pH 9.0.

Yield and purity after refolding: Properly folded Ranibizumab yield after refolding was around 18% of the total protein.

Example 6

Purification for Properly Folded Protein

Refolding output was concentrated using 10 kDa membrane and diafiltered against 50 mM Tris buffer pH 9.0. Diafiltration output was loaded on Q Sepharose FF resin in binding mode and protein was eluted out by reducing the pH to 6.7 in linear gradient in 10 CV from 0% B to 100% B. Q Sepharose Output was loaded on SP Sepharose HP resin at pH 5.0. Protein was eluted out by increasing salt concentration as follows 20% step followed by 20% to 50% gradient and finally a 100% step gradient. Pooled fractions were concentrated and diafiltered against the formulation buffer using a 10 kDa membrane.

Yield of final product after purification: The overall protein purification process recovery was around 9% with a purity level of >99%.

---

We claim:

1. A process for the preparation of Ranibizumab comprising steps of:
   a) transforming a first host cell with a first vector comprising a first polynucleotide encoding a signal sequence of SEQ ID NO: 5 operably linked to a light chain of Ranibizumab of SEQ ID NO: 2, wherein the first polynucleotide is operably linked to an inducible promoter system;
   b) transforming a second host cell with a second vector comprising a second polynucleotide encoding a signal sequence of SEQ ID NO: 6 operably linked to a heavy chain of Ranibizumab of SEQ ID NO: 4, for heavy chain of wherein the second polynucleotide is operably linked to an inducible promoter system;
   c) separately culturing the first host cell and the second host cell in a growth medium;
   d) expressing the light chain of Ranibizumab in the first host cell and the heavy chain of Ranibizumab in the second host cell as periplasmic inclusion bodies;
   e) solubilizing the inclusion bodies; and
   f) refolding in-vitro the solubilized light chain and heavy chain of Ranibizumab.

2. The process of claim 1, wherein the signal sequence of SEQ ID NO: 5 in the expressing step directs the first host cell to transport the light chain of Ranibizumab to a periplasmic space of the first host cell.

3. The process of claim 1, wherein the signal sequence of SEQ ID NO: 6 in the expressing step directs the second host cell to transport the heavy chain of Ranibizumab to a periplasmic space of the second host cell.

4. The process of claim 1, wherein the first host cell in the culturing step is cultured to an OD600 of about 50.

5. The process of claim 1, wherein the second host cell in the culturing step is cultured to an OD600 of about 100.

6. The process of claim 1, wherein the first polynucleotide is nt 8 to nt 718 of SEQ ID NO: 1.

7. The process of claim 1, wherein the second polynucleotide is nt 9 to nt 770 of SEQ ID NO: 3.

* * * * *

UNITED STATES PATENT AND TRADEMARK OFFICE
CERTIFICATE OF CORRECTION

PATENT NO. : 9,914,770 B2
APPLICATION NO. : 14/787981
DATED : March 13, 2018
INVENTOR(S) : Harish Shandilya et al.

Page 1 of 1

It is certified that error appears in the above-identified patent and that said Letters Patent is hereby corrected as shown below:

In the Claims

Column 17, Lines 49-50, Claim 1:
After "SEQ ID NO: 4"
Delete "for heavy chain of"

Signed and Sealed this
Seventh Day of August, 2018

Andrei Iancu
*Director of the United States Patent and Trademark Office*

SEQUENCE LISTING

```
<160> NUMBER OF SEQ ID NOS: 6

<210> SEQ ID NO 1
<211> LENGTH: 733
<212> TYPE: DNA
<213> ORGANISM: Artificial Sequence
<220> FEATURE:
<223> OTHER INFORMATION: vector having light chain of Ranibizumab

<400> SEQUENCE: 1
gagctccatg gagttttca aaaagacggc acttgccgca ctggttatgg gttttagtgg      60
tgcagcattg gccgatatcc agctgaccca gagcccgagc agcctgagcg caagcgttgg    120
tgatcgtgtt accattacct gtagcgcaag ccaggatatt agcaattatc tgaattggta    180
```

-continued

```
tcagcagaaa ccgggtaaag caccgaaagt tctgatttat tttaccagca gcctgcatag      240
cggtgttccg agccgtttta gcggtagcgg tagtggcacc gatttaccc tgaccattag       300 cagcctgcag ccggaagatt ttgcaaccta ttattgtcag cagtatagca ccgttccgtg      360
gacctttggt cagggcacca agttgaaat taaacgtacc gttgcagcac cgagcgtttt      420 tattttccg cctagtgatg aacagctgaa agcggcacc gcaagcgttg tttgtctgct       480
gaataatttt tatccgcgtg aagcaaaagt gcagtggaaa gttgataatg cactgcagag      540
cggtaatagc caagaaagcg ttaccgaaca ggatagcaaa gatagcacct atagcctgag      600
cagcaccctg accctgagca aagcagatta tgaaaaacac aaagtgtatg cctgcgaagt      660
tacccatcag ggtctgagca gtccggttac caaaagtttt aatcgtggcg aatgctaata      720
gaagcttggt acc                                                        733
```

```
<210> SEQ ID NO 2
<211> LENGTH: 214
<212> TYPE: PRT
<213> ORGANISM: Artificial Sequence
<220> FEATURE:
<223> OTHER INFORMATION: light chain of Ranibizumab

<400> SEQUENCE: 2
```

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 3
<211> LENGTH: 779
<212> TYPE: DNA
<213> ORGANISM: Artificial Sequence
<220> FEATURE:
```

<223> OTHER INFORMATION: vector having heavy chain of ranibizumab

<400> SEQUENCE: 3

```
gagctcatat gaaatacctg ctgccgaccg ctgctgctgg tctgctgctc ctcgctgccc      60
agccggcgat ggccgaagtt cagctggttg aaagcggtgg tggtctggtt cagcctggtg     120
gtagcctgcg tctgagctgt gcagcaagcg gttatgattt tacccattat ggtatgaatt     180
gggttcgtca ggcaccgggt aaaggtctgg aatgggttgg ttggattaat acctataccg     240
gtgaaccgac ctatgcagca gattttaaac gtcgttttac ctttagcctg dataccagca     300
aaagcaccgc atatctgcag atgaatagcc tgcgtgcaga agataccgca gtttattatt     360
gtgccaaata tccgtattac tatggcacca gccactggta tttcgatgtt tggggtcagg     420
gcaccctggt taccgttagc agcgcaagca ccaaaggtcc gagcgttttt ccgctggcac     480
cgagcagcaa aagtaccagc ggtggcacag cagcactggg ttgtctggtt aaagattatt     540
ttccggaacc ggttaccgtg agctggaata cggtgcact gaccagcggt gttcataccgt     600
ttccggcagt tctgcagagc agcggtctgt atagcctgag cagcgttgtt accgttccga     660
gcagcagcct gggcacccag acctatattt gtaatgttaa tcataaaccg agcaatacca     720
aagtggataa aaaagttgag ccgaaaagct gcgataaaac ccatctgtaa tagggtacc     779
```

<210> SEQ ID NO 4
<211> LENGTH: 231
<212> TYPE: PRT
<213> ORGANISM: Artificial Sequence
<220> FEATURE:
<223> OTHER INFORMATION: heavy chain of ranibizumab

<400> SEQUENCE: 4

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Asp Phe Thr His Tyr
                 20                  25                  30

Gly Met Asn Trp Val Arg Gln Ala Pro Gly Lys Gly Leu Glu Trp Val
             35                  40                  45

Gly Trp Ile Asn Thr Tyr Thr Gly Glu Pro Thr Tyr Ala Ala Asp Phe
         50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro Tyr Tyr Gly Thr Ser His Trp Tyr Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

```
Asn His Lys Pro Ser Asn Thr Lys Val Asp Lys Lys Val Glu Pro Lys
    210                 215                 220

Ser Cys Asp Lys Thr His Leu
225                 230

<210> SEQ ID NO 5
<211> LENGTH: 22
<212> TYPE: PRT
<213> ORGANISM: Artificial Sequence
<220> FEATURE:
<223> OTHER INFORMATION: signal sequence linked to light chain of
      Ranibizumab

<400> SEQUENCE: 5

Met Glu Phe Phe Lys Lys Thr Ala Leu Ala Ala Leu Val Met Gly Phe
1               5                   10                  15

Ser Gly Ala Ala Leu Ala
            20

<210> SEQ ID NO 6
<211> LENGTH: 22
<212> TYPE: PRT
<213> ORGANISM: Artificial Sequence
<220> FEATURE:
<223> OTHER INFORMATION: signal sequence linked to heavy chain of
      ranibizumab

<400> SEQUENCE: 6

Met Lys Tyr Leu Leu Pro Thr Ala Ala Ala Gly Leu Leu Leu Leu Ala
1               5                   10                  15

Ala Gln Pro Ala Met Ala
            20
```